(12) United States Patent
Pepper

(10) Patent No.: US 6,395,033 B1
(45) Date of Patent: May 28, 2002

(54) DYNAMIC FUSION MECHANOSTAT DEVICES

(75) Inventor: John R. Pepper, Cheshire, CT (US)

(73) Assignee: Tyco Healthcare Group LP, Norwalk, CT (US)

(*) Notice: Subject to any disclaimer, the term of this patent is extended or adjusted under 35 U.S.C. 154(b) by 0 days.

(21) Appl. No.: 09/545,949

(22) Filed: Apr. 10, 2000

(51) Int. Cl.[7] .................................................. A61F 2/44
(52) U.S. Cl. ..................... 623/17.13; 606/61; 623/23.32
(58) Field of Search .......................... 623/17.13, 23.32, 623/23.58, 23.75; 606/60, 61

(56) References Cited

U.S. PATENT DOCUMENTS

| | | | | |
|---|---|---|---|---|
| 4,309,777 A | * | 1/1982 | Patil ............................ | 623/17.13 |
| 4,512,038 A | * | 4/1985 | Alexander et al. ........ | 623/23.75 |
| 4,781,183 A | * | 11/1988 | Casey et al. ............... | 606/76 |
| 4,863,472 A | * | 9/1989 | Tomala et al. ............. | 623/16 |
| 4,888,413 A | * | 12/1989 | Domb ......................... | 528/272 |
| 5,423,816 A | * | 6/1995 | Lin .............................. | 606/61 |
| 5,433,751 A | * | 7/1995 | Christel et al. ............ | 623/16 |
| 5,458,642 A | * | 10/1995 | Beer et al. .................. | 623/17 |
| 5,522,895 A | * | 6/1996 | Mikos ......................... | 623/16 |
| 5,672,175 A | * | 9/1997 | Martin ........................ | 606/61 |
| 5,704,937 A | * | 1/1998 | Martin ........................ | 606/61 |
| 5,827,328 A | * | 10/1998 | Buttermann ................ | 623/17 |
| 5,928,824 A | * | 7/1999 | Mehdizadeh ............... | 623/17 |
| 6,013,853 A | * | 1/2000 | Athanasiou et al. ....... | 623/11 |
| 6,068,630 A | * | 5/2000 | Zucherman et al. ....... | 606/61 |
| 6,090,996 A | * | 7/2000 | Li ................................ | 623/11 |
| 6,206,883 B1 | * | 3/2001 | Tunc .......................... | 606/77 |

* cited by examiner

Primary Examiner—Nicholas D. Lucchesi
Assistant Examiner—Michael B. Priddy

(57) ABSTRACT

A dynamic bone fusion device for facilitating fusion between bone sections, particularly vertebrae, is selected having certain stiffness to induce specific strain conditions associated with high success rates in bone fusion. Temporary stiffeners that are absorbable by the body may be implemented with the fusion device.

8 Claims, 3 Drawing Sheets

- ~<4% STRAIN   INTRAMEMBRANOUS BONE

- ~<4 TO 15%   ENDOCHODRAL OSSIFICATION

- ~>15%   CONNECTIVE TISSUE

FIG_1

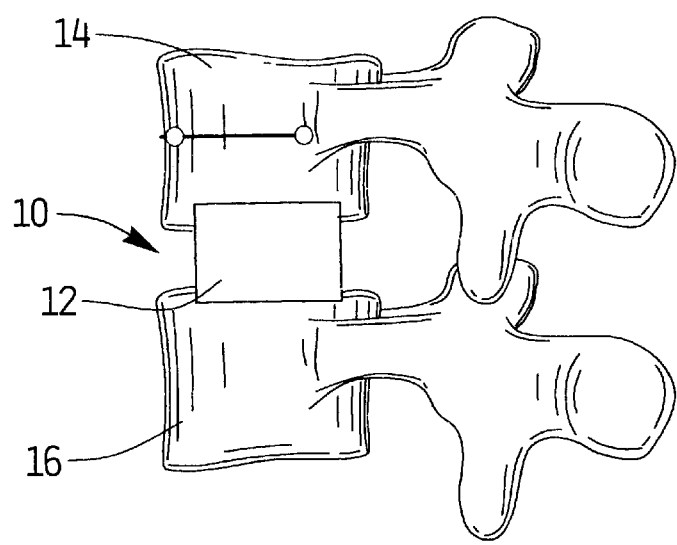
FIG_2
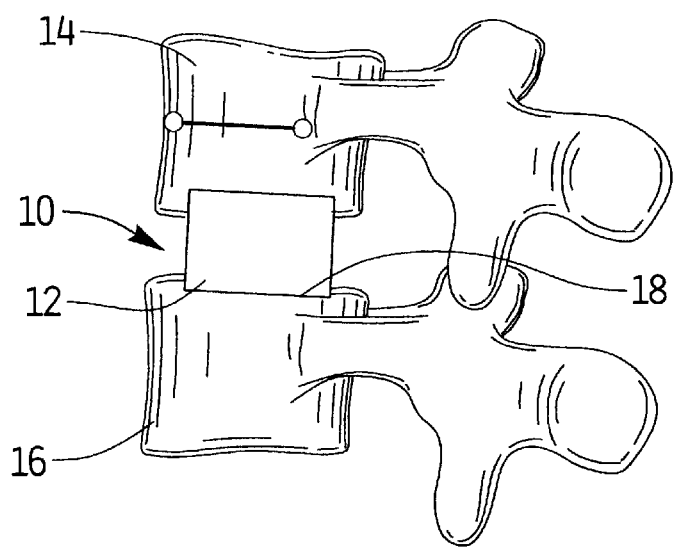
FIG_4

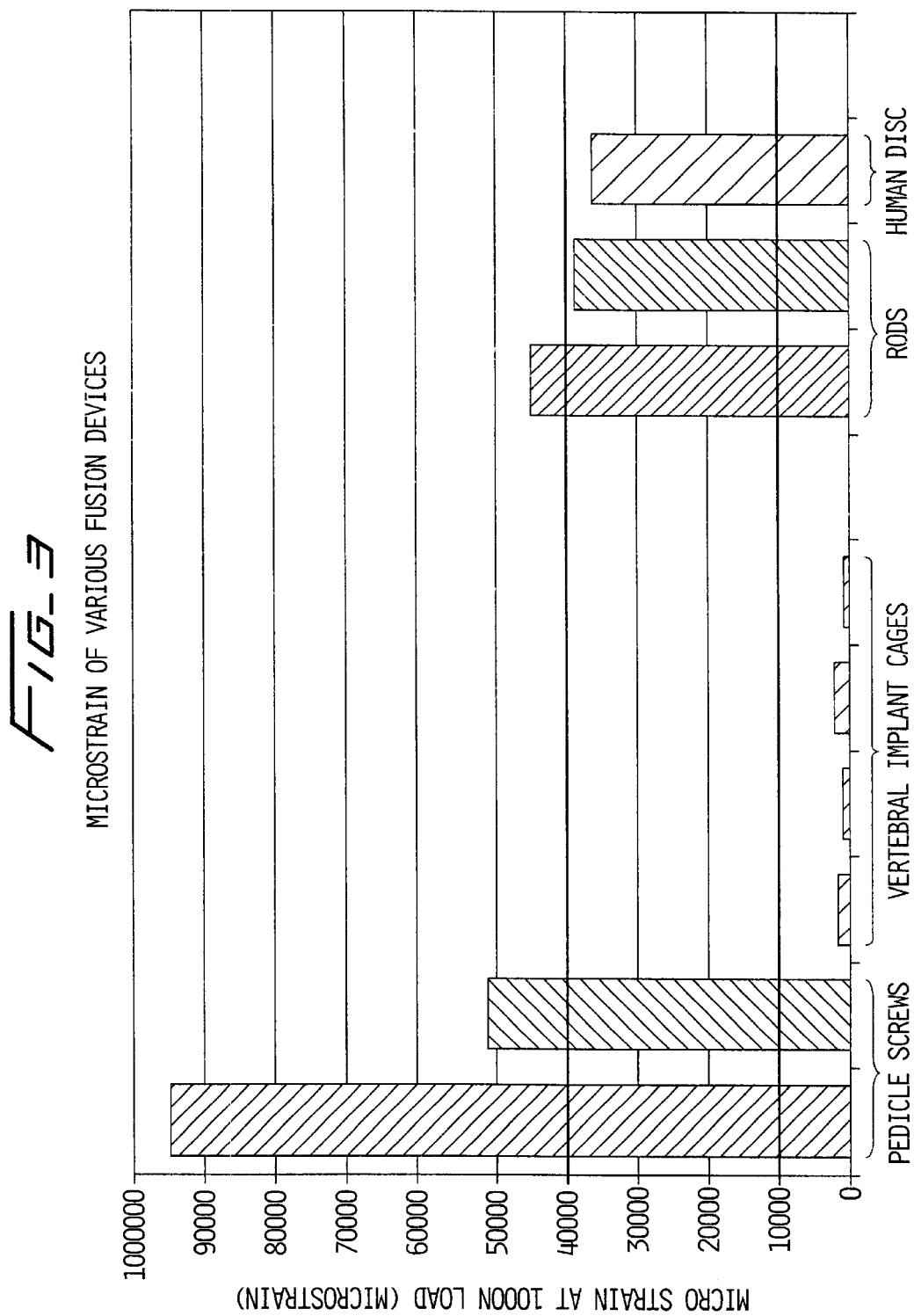

DYNAMIC FUSION MECHANOSTAT DEVICES

TECHNICAL FIELD OF THE INVENTION

The present invention relates to dynamic bone fusion devices and associated techniques and, more particularly, to such fusion devices and associated techniques for effecting optimal spinal fusion.

BACKGROUND OF THE INVENTION

It is known generally that, according to Wolff's law, every change in the form and function of a bone, or in its function alone, is followed by certain definite changes in its internal architecture and secondary alterations in its external conformation.[1] Based on this principle and others, dynamic bone fusion devices and procedures are designed to simulate strain conditions in which compressive forces are applied to the junction of bone segments to be fused, thereby initiating and sustaining fusion.

[1]Stedman's Medical Dictionary, 26$^{th}$ Ed, 1995

The success rates of fusion depend on a variety of factors including the location and types of bones to be fused, and the techniques and devices used. There currently does not exist specific available data and correlating guidelines on the types of devices and techniques that, for a given set of parameters, provides ideal or optimum strain or loading conditions to initiate and sustain high success rate dynamic fusion. Nor does there currently exist specific available data for identifying ideal strain and loading conditions for vertebral dynamic fusion.

SUMMARY OF THE INVENTION

It is an object of the present invention to provide devices and associated techniques for initiating and sustaining optimum dynamic bone fusion procedures and, particularly, such procedures for vertebral fusion. These objects and others are achieved by the present invention described herein.

The present invention is directed to dynamic fusion devices, such as spinal implant devices for vertebral fusion, that are selected within the parameters of available data and modeling to determine optimum ranges of strain and loading for initiating and sustaining highly successful rates of fusion. In summary, various available data for a variety of fusion cases has been analyzed and is used as a basis for modeling the fusion conditions of vertebrae. Specifically, data available from intra medullary nail systems is used with beam deflection principles to arrive at stiffness constants and applicable strain conditions for ideal states in which high fusion success rates are likely.

BRIEF DESCRIPTION OF THE DRAWINGS

FIG. 1 is a table illustrating bone fusion strain ranges and corresponding ossification characteristics.

FIG. 2 is a schematic, side view of an intervertebral dynamic fusion device implanted between adjacent vertebrae according to the present invention.

FIG. 3 is a table illustrating strain properties associated with typical bone fusion devices.

FIG. 4 is a schematic, side view of an intervertebral dynamic fusion device implanted between adjacent vertebrae and having absorbable stiffening elements according to the present invention.

DESCRIPTION OF THE PREFERRED EMBODIMENT

Applying Wolff's Law and analyzing data from various studies on bone mechanostat reaction to various strain rates, the present invention dynamic fusion device and its properties can be modeled. An active zone for achieving successful rates of bone fusion is generally in the range of 0.0008–0.002 unit bone surface strain.[2] Microstrains of 1700 have been used to perform studies on cell response to mechanical stimuli.[3] Differences in mediators at rates of 200, 400 and 1000 microstrain have been observed.[4] Data from tests applying a spatially uniform biaxial strain (1.3% applied strain) have been analyzed.[5]

[2]Frost, H. M., Clin Orthop May 1983, 286–92
[3]Brighton et al., J Bone Joint Surg Am, Sep 1986, 78(9): 1337–47
[4]Brighton, JBJS 73A, Mar 1991, 320
[5]Toma, J Bone Miner Res, Oct. 12 1997, 1626–36

The highest strains were observed during distraction osteogenesis. Average maximum cyclic strains within the distraction zone during ambulation were estimated to be between 14% and 15%, and supported using fluoroscope imaging. These strains are higher than would be expected in spinal fusion, and thus serve as a high end limit for modeling.[6] Magnitudes of local strain are indicative of the type of fracture healing.[7] As shown in FIG. 1, up to 4% strain had more osteoblast proliferation than non-strained bone. Intramembranous bone formation was found for strains smaller than approximately 5% and small hydrostatic pressure. Strains less than 15% and hydrostatic pressure more than 0.15 MPa stimulated endochondral ossification. Larger strains led to connective tissue.[8]

[6]Waanders et al., Clin Orthop, Apr 1993, (349) 225–34
[7]Claes, J Biomech, Mar 1999, 32(3): 255–66
[8]Claes, Clin Orthop, Oct 1998, (355 Suppl) S132–47

The strain-related variable which had the greatest influence on every remodeling parameter investigated was the ratio between the maximum strain rate of the artificial regime and the maximum strain rate during walking, or ambulation. The variation in this ratio accounts for approximately 70%–80% of the variation in the measurement of surface bone deposit.[9]

[9]O'Conner et al., J Biomech, 1982, 15(10): 767–81

As a result of test data analysis and modeling using basic beam deflection equations for medullar nail systems, it is determined that the best range of strain for initiating and sustaining vertebral fusion between adjacent vertebrae for a dynamic fusion device (10) implanted between adjacent vertebrae (14, 16) as shown schematically in FIG. 2, is 4–8%. Depending on other various factors including patient condition, the range may be expanded to 2–10% and, in less critical instances 0.5–15%. A schematic spring element (12) represents the stiffness constant element.

Shown in FIG. 3, is a strain graph for various commercially available products including pedicle screws, vertebral implant cages, and long bone rods. Also included is the strain for a typical vertebral disc. As shown, the existing vertebral implants are outside of the target range of 0.5–15% strain, and certainly outside of the optimal range of 4–8%.

The target or optimal ranges may be achieved by selecting dynamic fusion device materials and geometries that, together with physical parameters of the patient, create the ideal strain conditions identified above. As shown schematically in FIG. 4, a dynamic fusion device (10) for implanting between adjacent vertebrae (14, 16) to be fused can be provided with compressive spring characteristics (12) along a vertical axis. Optionally, performance may be enhanced with features that initially maintain the stiffness of the device and gradually reduce overall stiffness. For example, polylactic acid inserts (18) designed to absorb after a predetermined time may be used to bolster the dynamic fusion device, adding stiffness and gradually reducing overall stiffness. Such a feature will, in appropriate instances, withhold excessive loading while ossification initiates and, after a desired period, increase the loading.

While the preferred embodiment has been herein disclosed, it is understood and acknowledged that variation and modification to the preferred embodiment may be made without departing from the scope of the present invention.

What is claimed is:

1. An intervertebral dynamic bone fusion device for dynamically supporting adjacent upper and lower vertebrae to be fused, said device comprising:

a spring element positionable within an intervertebral space defined between the adjacent upper and lower vertebrae and having a height slightly greater than the height of the intervertebral space, the spring element adapted to generally linearly oppose the adjacent upper and lower vertebrae, said spring element having a spring constant selected to create a strain range between the adjacent upper and lower vertebrae, said strain range ranging from about 4% to about 8%.

2. A fusion device according to claim 1, further comprising a temporary stiffening element adapted to cooperate with said fusion device to enhance its stiffness in the direction of said compressive forces, said stiffening element being absorbable into a body of a patient after a predetermined time period.

3. A dynamic bone fusion device for dynamically supporting adjacent upper and lower vertebrae, which comprises:

a spring element positionable within an intervertebral space defined between the adjacent upper and lower vertebrae and having a height in an uncompressed condition thereof greater than the height of the intervertebral space, the spring element adapted to generally linearly oppose compressive forces between the adjacent upper and lower vertebrae: and a temporary stiffening element associated with the spring element and adapted to increase stiffness in the direction of the compressive forces, the stiffening element comprising a bioabsorbable material which is gradually fully absorbed after a predetermined period of time.

4. The dynamic fusion device of claim 3 wherein the spring element and the temporary stiffening element define a spring constant, the spring constant adapted to provide a strain range between the adjacent upper and lower vertebrae sufficient to initiate and sustain fusion between the adjacent vertebrae.

5. The dynamic fusion device of claim 4 wherein the strain range ranges from about 4% to about 8%.

6. A method for facilitating fusion of adjacent upper and lower vertebrae, comprising the steps of:

accessing an intervertebral space defined between adjacent upper and lower vertebral bone tissues; and positioning a bone fusion device within the intervertebral space, the bone fusion device having a spring constant sufficient to support the adjacent vertebral bone tissues in spaced relation and creating a strain range between the adjacent upper and lower vertebral bone tissues sufficient to initiate and sustain ossification and fusion thereof.

7. The method of claim 6 wherein the bone fusion device defines a spring constant which creates a strain range ranging from about 4% to about 8%.

8. The method according to claim 6 wherein the bone fusion device includes a spring member and a bioabsorbable member, and further including the step of permitting the bioabsorbable member to gradually absorb to gradually increase a load exerted on the spring member.

* * * * *